United States Patent [19]

Ernst

[11] Patent Number: 4,879,420
[45] Date of Patent: Nov. 7, 1989

[54] PREPARATION OF MIXTURES OF BUTANEDIOLS

[75] Inventor: Richard E. Ernst, Kennett Square, Pa.

[73] Assignee: E.I. du Pont de Nemours and Company, Wilmington, Del.

[21] Appl. No.: 190,907

[22] Filed: May 6, 1988

[51] Int. Cl.$^4$ .................... C07C 29/38; C07C 31/20; C07C 41/00; C07D 307/02

[52] U.S. Cl. .................................... 568/617; 549/509; 568/862

[58] Field of Search ................. 568/862, 617; 549/509

[56] References Cited

U.S. PATENT DOCUMENTS 2,572,941 10/1951 MacLean et al. ................... 568/862
3,290,387 12/1966 Bernardy et al. ................... 568/862

Primary Examiner—J. E. Evans
Attorney, Agent, or Firm—Charles E. Feeny

[57] ABSTRACT

Process for preparing 2-alkyl-1,4-butanediols and mixtures with 1,4-butanediol which comprises bringing together, at an initial alkaline pH, and at a temperature and pressure suitable for reaction, a mixture of 4-hydroxybutyraldehyde and/or its cyclic acetal, 2-hydroxytetrahydrofuran, hydrogen, an unsubstituted aliphatic aldehyde, especially formaldehyde, and a hydrogenation catalyst. Also processes for preparing mixtures of tetrahydrofuran and 3-alkyltetrahydrofuran from the diol mixtures, and copolymers from the tetrahydrofuran mixtures.

18 Claims, No Drawings

PREPARATION OF MIXTURES OF BUTANEDIOLS

FIELD OF THE INVENTION

This invention relates to a process for preparation of 2-alkyl-1,4-butanediols from 4-hydroxybutyraldehyde and/or its cyclic hemiacetal.

BACKGROUND OF THE INVENTION

The 2-alkyl-1,4-butanediols, especially 2-methyl-1,4-butanediol, have a variety of uses. For example, they can be cyclized to the corresponding 3-alkyltetrahydrofurans. Amongst other uses, 3-alkyltetrahydrofurans can be copolymerized with tetrahydrofuran to form polyether glycols, and those glycols can be used in preparing polyurethane elastomers. In the past, 2-alkyl-1,4-butanediols have been prepared by a variety of techniques. For example, they have been prepared by the reduction of itaconic acid. They have also been prepared by the hydroformylation of 1,4-butenediol followed by hydrogenation of the hydroformylation reaction product (believed to be 2-formyl-1,4-butanediol), as described by Copelin in U.S. Pat. No. 3,859,369. In addition, they have been prepared by catalytic hydrogenation of 1,4-butynediol or 1,4-butenediol in the presence of an aldehyde as disclosed in my U.S. Pat. No. 4,590,312.

While the prior art methods are useful, they are not without their disadvantages. Itaconic acid and the acetylene-based chemicals used in prior art processes are expensive, and there is thus a need for a process which can be operated at a lower cost. In some of the prior art processes, production of 2-alkyl-1,4-butanediols is accompanied by the production of 1,4-butanediol. Those prior art methods yield a greater quantity of 1,4-butanediol than the 2-alkyl-1,4-butanediols. For example, the process disclosed and claimed in my U.S. Pat. No. 4,590,312 gives a diol mixture having a maximum 2-alkyl-1,4-butanediol content of about 15 percent by weight. While that may at times be the desired result, at other times it is desirable to prepare mixtures of 2-alkyl-1,4-butanediols and 1,4-butanediol which contain more of the former than the latter.

BRIEF SUMMARY OF THE INVENTION

The process of this invention overcomes the disadvantages of the prior art. It relates to a process for the synthesis of 2-alkyl-1,4-butanediols by reacting 4-hydroxybutyraldehyde and/or its cyclic hemiacetal, 2-hydroxytetrahydrofuran, with a mixture of an aldehyde and hydrogen in the presence of a catalyst. It relates also to processes for the preparation of 3-alkyltetrahydrofuran and polymers therefrom.

DETAILED DESCRIPTION OF THE INVENTION

The diol synthesis process of this invention can be carried out by bringing together, at an initial alkaline pH and at a temperature and pressure suitable for reaction, a mixture of 4-hydroxybutyraldehyde and/or its cyclic acetal, 2-hydroxytetrahydrofuran, with which it ordinarily exists as an equilibrium mixture, hydrogen, an unsubstituted aliphatic aldehyde, and a hydrogenation catalyst. The diol synthesis process of this invention is not limited by any particular theory of operation; however, it is believed that the following reactions may take place while it is being carried out:

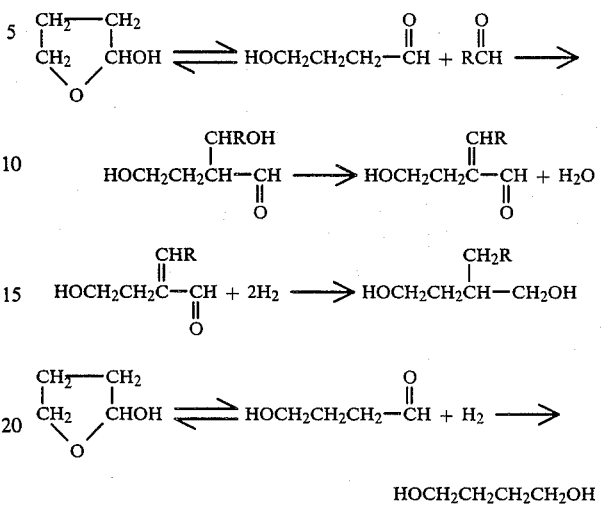

wherein R is hydrogen or an alkyl radical of 1–4 carbon atoms, preferably methyl.

The product of the diol synthesis process of this invention is a mixture, the organic portion of which, is composed predominantly of 1,4-butanediol and 2-alkyl-1,4-butanediol together with small amounts of low molecular weight alcohols and unidentified high boilers. One of the advantages of the process of this invention is its capacity to provide a diol product mixture having a high 2-alkyl-1,4-butanediol content. For example, products having a diol content made up of 75 percent by weight of the 2-alkyl-1,3-butanediol and 25 percent by weight of 1,4-butanediol have been prepared in accordance with the process of this invention. On the other hand, one of the other advantages of the process of this invention is its flexibility. Thus one can prepare a diol product mixture which contains less 2-alkyl-1,4-butanediol than 1,4-butanediol, either by using less of the aldehyde or less of the base used to provide the alkaline pH under which the process is run.

The 2-alkyl-1,4-butanediol and 1,4-butanediol can be separated from one another by conventional procedures. On the other hand, it is sometimes desirable to keep the mixture intact, for the mixture of diols can be cyclized in one step to give a mixture of a 3-alkyltetrahydrofuran and tetrahydrofuran. In addition, a copolymer can be prepared directly from the resulting mixture of a 3-alkyltetrahydrofuran and tetrahydrofuran by adding to the mixture of tetrahydrofurans a polymerization catalyst under conditions effective for polymerization.

The diol synthesis process of this invention can be run either in batch or continuous mode. In either mode, suitable hydrogenation catalysts such as, platinum, Raney nickel or cobalt can be used. The preferred catalyst for the preparation of the mixture of diols of this invention is Raney nickel. It can be in the form of a finely divided slurry catalyst (from which most of the aluminum has been removed) for use in a slurry reactor, or in granular form (from which about 25% by weight of the aluminum has been removed) for use in a fixed bed reactor.

When a 4-hydroxybutyraldehyde/2-hydroxytetrahydrofuran (4-HBA/2-HTF) mixture is used as a starting material, it can be prepared by a variety of methods. For example, it can be that obtained either by the hydrolysis of 2,3-dihydrofuran as described in *Bull. Soc. Chim. France* 1950, 668–71, or it can be prepared by the hydroformylation of allyl alcohol as disclosed in U.S. Pat. No. 4,567,305. The products obtained by either of those methods can be concentrated or isolated before use in this invention, but more conveniently the reaction masses containing the product 4-HBA/2-HTF mixture is used without further treatment. The unsubstituted aliphatic aldehyde is ordinarily added to the reaction mass as an aqueous solution. Formaldehyde is the preferred aldehyde for use in the process of this invention. Enough is used to provide a 4-HBA/2-HTF:unsubstituted aliphatic aldehyde weight ratio of between about 2:1 and 200:1, preferably between about 10:1 and 25:1.

The pH of the combined reaction mass before contact with hydrogen (i.e. the initial pH) is adjusted to the range between about 8 and 14, preferably between about 10 and 12. The reaction can be carried out in the batch mode in a pressure vessel with some provision for agitation. A shaker tube is convenient. The mass is hydrogenated at about 6,895 to 55,160 kPa (gauge) hydrogen, preferably at about 34,475 kPa, for about 30 to 200 minutes, preferably about 100 to 200 minutes, at temperatures in the range between about 100° and 200° C., preferably at about 140° to 180° C. The process of this invention can also be run in the continuous mode in a column reactor of appropriate dimensions, using basically the same conditions and proportions of reactants as described above for batch operation. The catalyst should preferably be granular. Hydrogen can be fed either co-current or counter current to the other reactants and the temperature can be controlled by recycling the reaction mass. That type of continuous mode operation is described in more detail in my U.S. Pat. No. 4,590,285, the contents of which are incorporated herein by reference.

In another embodiment of the present invention, the mixture of 2-alkyl-1,4-butanediol and 1,4-butanediol produced by the diol synthesis process of this invention is catalytically cyclized to a mixture of the corresponding 3-alkyltetrahydrofuran and tetrahydrofuran, using sulfuric acid as the catalyst, according to the process disclosed by Coates et al. in U.S. Pat. No. 3,726,905. In yet another embodiment of the present invention, the resulting mixture of tetrahydrofurans is copolymerized in the presence of a fluosulfonic acid catalyst to form a tetrahydrofuran/-3-alkyltetrahydrofuran copolymer in accordance with the process disclosed by Dunlap et al. in U.S. Pat. No. 3,358,042. The resulting copolymer can then be used to prepare a polyurethane in accordance with the method disclosed by Pechhold in U.S. Pat. No. 4,120,850. (The contents of each of the foregoing Coates et al., Dunlap et al. and Pechhold patents are incorporated herein by reference.)

The following examples further illustrate the present invention. Unless indicated otherwise, all parts, ratios and percentages are by weight and all temperatures are in degrees Celsius.

EXAMPLE 1

The 4-hydroxybutyraldehyde/2-hydroxytetrahydrofuran was prepared by adding 20 parts of 2,3-dihydrofuran to 10 parts of 2% $H_2SO_4$ over about 20 minutes, keeping the temperature at 35° with cooling. The mixture was then neutralized with 30% NaOH. The organic portion of the resulting homogeneous product was a 2:1 mixture of 4-hydroxybutyraldehyde and its cyclic hemiacetal, 2-hydroxytetrahydrofuran. Thirty parts of that mixture were mixed with 10 parts of water, 4.3 parts of 37% aqueous formaldehyde, 0.53 parts of 30% NaOH, and 2 parts of Raney nickel. Hydrogenation was then carried out at 27,576 kPa (gauge) hydrogen at 150° for 2 hours in a shaker tube. The organic portion of the resulting product consisted mainly of 1,4-butanediol and 2-methyl-1,4-butanediol, in a ratio of 55:45. There were also some unidentified higher boilers.

EXAMPLE 2

The 4-hydroxybutyraldehyde/2-hydroxytetrahydrofuran was prepared by adding 5 parts of 2,3-dihydrofuran to 10 parts of 2% $H_2SO_4$ over about 20 minutes, keeping the temperature at 35° with cooling. The mixture was then neutralized with 30% NaOH. That mixture was mixed with 25 parts of water, 4.3 parts of 37% aqueous formaldehyde, 0.53 parts of 30% NaOH, and 2 parts of Raney nickel. Hydrogenation was then carried out at 27,576 kPa (gauge) hydrogen at 150° for 2 hours in a shaker tube. The organic portion of the resulting product consisted mainly of 1,4-butanediol and 2-methyl-1,4-butanediol, in a ratio of 25:75. There were also some unidentified higher boilers.

EXAMPLE 3

The 4-hydroxybutyraldehyde/2-hydroxytetrahydrofuran was prepared by the process described below (see U.S. Pat. No. 4,567,305). A solution of 23.6 parts of allyl alcohol, 0.044 parts of $Rh_6(CO)_{16}$, 9.36 parts of triphenylphosphine and 0.02 parts of 1,4-bis(diphenylphosphino)butane in 208 parts of toluene were reacted under 349 kPa of $H_2/CO$ (1:1) at 60° for 6 hours. The resulting mixture was extracted three times with a total 240 parts of water. Forty parts of the aqueous extract (containing the 4-hydroxybutyraldehyde and 2-hydroxytetrahydrofuran) were mixed with 4.3 parts of 37% aqueous formaldehyde, 0.53 parts of 30% NaOH, and 2 parts of Raney nickel slurry catalyst. This solution, which had a pH of 10.3, was subjected at 150° to hydrogenation, 27,576 kPa $H_2$, for 2 hours. Of the diols in the resulting mixture, 42% was 1,4-butanediol, 53% was 2-methyl-1,4-butanediol, and 5% was 2-methyl-1,3-propanediol.

A sample of the mixture of diols and water produced in the reaction was concentrated by distilling off most of the water until the pot temperature reached 130° (leaving about 5% water). Sufficient concentrated sulfuric acid was added to give a sulfuric acid content of 3%, and the mixture was heated at 130°, allowing tetrahydrofurans and water to distill overhead. (The 2-methyl-1,3-propanediol remained in the pot as it did not cyclize) After about half of the mixture had been cyclized, of the tetrahydrofurans in the resulting product, 61% was 3-methyl tetrahydrofuran and 39% was tetrahydrofuran.

COMPARATIVE EXAMPLE 1

The 4-hydroxybutyraldehyde prepared as in U.S. Pat. No. 4,567,305 was hydrogenated at pH 10 under the same conditions as in Example 3, but without the addition of formaldehyde. Of the diols in the resulting product, 90% was 1,4-butanediol, 9% was 2-methyl-1,3-propanediol, and 1% was 2-methyl-1,4-butanediol.

I claim:

1. A process for the preparation of 2-alkyl-1,4-butanediols which comprises bringing together, at an initial alkaline pH, and at a temperature and pressure effective for reaction, a mixture of:
   (a) 4-hydroxybutyraldehyde, 2-hydroxy tetrahydrofuran, or a mixture of the same,
   (b) hydrogen,
   (c) an unsubstituted aliphatic aldehyde, and
   (d) a hydrogenation catalyst.

2. A process for preparing a 2-alkyl-1,4-butanediol comprising
   (a) bringing together at an initial pH in the range between about 8 and 14 and a temperature and pressure effective for reaction:
      (i) hydrogen,
      (ii) a hydrogenation catalyst,
      (iii) 4-hydroxybutyraldehyde, 2-hydroxy tetrahydrofuran, or a mixture of the same, and
      (iv) an aldehyde of the structure

R—CHO wherein R is hydrogen or an alkyl radical of containing 1 to 4 carbon atoms,
   in a 4-hydroxybutyraldehyde/2-hydroxytetrahydrofuran: aldehyde weight ratio in the range between about 2:1 to 200:1, and
   (b) then separating the resulting 2-alkylbutanediol from the reaction mass.

3. The process of claim 2 wherein said aldehyde is formaldehyde.

4. The method of claim 3 wherein said weight ratio is between about 10:1 and 25:1.

5. The method of claim 4 wherein said pH is in the range between about 10 and 12.

6. A process for the preparation of a mixture of 1,4-butanediol and a 2-alkyl-1,4-butanediol which comprises bringing together, at an initial alkaline pH, and at a temperature and pressure effective for reaction, a mixture of:
   (a) 4-hydroxybutyraldehyde, 2-hydroxy tetrahydrofuran, or a mixture of the same,
   (b) hydrogen,
   (c) an unsubstituted aliphatic aldehyde, and
   (d) a hydrogenation catalyst.

7. A process for preparing a mixture of 1,4-butanediol and a 2-alkyl-1,4-butanediol comprising bringing together at an initial pH in the range between about 8 and 14, and a temperature and pressure effective for reaction:
   (a) hydrogen,
   (b) a hydrogenation catalyst,
   (c) 4-hydroxybutyraldehyde, 2-hydroxytetrahydrofuran or a mixture of the same, and
   (d) an aldehyde of the structure

R—CHO wherein R is hydrogen or an alkyl radical containing 1 to 4 carbon atoms,
   in a 4-hydroxybutyraldehyde/2-hydroxytetrahydrofuran: aldehyde weight ratio in the range between about 2:1 and 200:1.

8. The process of claim 7 wherein said aldehyde is formaldehyde.

9. The process of claim 8 wherein said weight ratio is between about 10:1 and 25:1.

10. The process of claim 9 wherein said pH is in the range between about 10 and 12.

11. In a process for preparing a mixture of tetrahydrofuran and 3-alkyltetrahydrofuran by cyclizing diols, the improvement comprising using as the diol starting material the mixture of 1,4-butanediol and 2-alkyl-1,4-butanediol prepared in accordance with the process of claim 7.

12. In a process for preparing a mixture of tetrahydrofuran and 3-methyltetrahydrofuran by cyclizing diols, the improvement comprising using as the diol starting material the mixture of 1,4-butanediol and 2-methyl-1,4-butanediol prepared in accordance with the process of claim 8.

13. In a process for preparing a mixture of tetrahydrofuran and 3-methyltetrahydrofuran by cyclizing diols, the improvement comprising using as the diol starting material the mixture of 1,4-butanediol and 2-methyl-1,4-butanediol prepared in accordance with the process of claim 9.

14. In a process for preparing a mixture of tetrahydrofuran and 3-methyltetrahydrofuran by cyclizing diols, the improvement comprising using as the diol starting material the mixture of 1,4-butanediol and 2-methyl-1,4-butanediol prepared in accordance with the process of claim 10.

15. In a process for preparing a copolymer from a mixture of tetrahydrofuran and 3-alkyltetrahydrofuran, the improvement comprising adding a polymerization catalyst to the mixture of tetrahydrofuran and 3-alkyltetrahydrofuran produced in accordance with the process of claim 11 and holding the resulting mixture under conditions effective for polymerization.

16. In a process for preparing a copolymer from a mixture of tetrahydrofuran and 3-methyltetrahydrofuran, the improvement comprising adding a polymerization catalyst to the mixture produced in accordance with the process of claim 12 and holding the resulting mixture under conditions effective for polymerization.

17. In a process for preparing a copolymer from a mixture of tetrahydrofuran and 3-methyltetrahydrofuran, the improvement comprising adding a polymerization catalyst to the mixture produced in accordance with the process of claim 13 and holding the resulting mixture under conditions effective for polymerization.

18. In a process for preparing a copolymer from a mixture of tetrahydrofuran and 3-methyltetrahydrofuran, the improvement comprising adding a polymerization catalyst to the mixture produced in accordance with the process of claim 14 and holding the resulting mixture under conditions effective for polymerization.

* * * * *